United States Patent [19]

Shimoyama et al.

[11] Patent Number: 5,929,292
[45] Date of Patent: Jul. 27, 1999

[54] DISTILLATION COLUMN TYPE PRODUCTION METHOD

[75] Inventors: Toru Shimoyama; Kazuya Oharu; Toru Ueno, all of Yokohama; Seisaku Kumai, Chigasaki, all of Japan

[73] Assignee: Asahi Glass Company Ltd., Tokyo, Japan

[21] Appl. No.: 08/870,303

[22] Filed: Jun. 6, 1997

[30] Foreign Application Priority Data

Jun. 6, 1996 [JP] Japan ................................. 8-144695
Aug. 15, 1996 [JP] Japan ................................. 8-215810

[51] Int. Cl.$^6$ .................................................. C07C 31/38
[52] U.S. Cl. ......................... 568/842; 568/850; 203/38
[58] Field of Search .................... 568/842, 850; 203/38

[56] References Cited

U.S. PATENT DOCUMENTS

| 2,559,628 | 7/1951 | Joyce . | |
|---|---|---|---|
| 4,346,250 | 8/1982 | Satokawa | 568/842 |
| 5,227,540 | 7/1993 | Knaup . | |
| 5,260,494 | 11/1993 | Pagniez | 568/842 |
| 5,557,017 | 9/1996 | Oharu et al. . | |
| 5,618,986 | 4/1997 | Oharu et al. . | |

FOREIGN PATENT DOCUMENTS

| 0 473 053 | 3/1992 | European Pat. Off. . |
|---|---|---|
| 0 487 264 | 5/1992 | European Pat. Off. . |

*Primary Examiner*—Gary Geist
*Assistant Examiner*—Jean F. Vollano
*Attorney, Agent, or Firm*—Oblon, Spivak, McClelland, Maier & Neustadt, P.C.

[57] ABSTRACT

A production method which comprises reacting one or more feedstock compounds to form a desired compound having a boiling point higher than the feedstock compounds, wherein the reaction is carried out under reflux in a distillation column portion of a reactor provided with the distillation column.

16 Claims, No Drawings

DISTILLATION COLUMN TYPE PRODUCTION METHOD

The present invention relates to a novel distillation column type production method wherein a reaction is carried out in a distillation column portion.

As an industrial method for producing a desired compound having a high boiling point from a feedstock compound having a low boiling point, it has been common to employ a method for separating the desired compound produced by a reactor by means of a distillation column.

Further, as a method for producing a polyfluoroalkyl alcohol of the formula $R^F(CH_2)_2CH(R^{10})$—OH (wherein $R^F$ is a $C_{1-20}$ polyfluoroalkyl group, and $R^{10}$ is a hydrogen atom or a $C_{1-5}$ alkyl group), there have been proposed (1) a method wherein a pressure reactor is used, and $R^FCH=CH_2$, an alkanol and a free radical initiator are charged all at once for reaction, and (2) a method wherein an alkanol is charged into a pressure reactor, and then $R^FCH=CH_2$ and a free radical initiator are continuously added (U.S. Pat. No. 5,227,540).

Still further, as a method for producing a perfluoroalkyl iodide, it is common to employ a method of telomerization of perfluoroethyl iodide or perfluoroisopropyl iodide with tetrafluoroethylene. As a method for the telomerization, (3) a method wherein the telomerization is carried out in the presence of a free radical initiator (U.S. Pat. No. 3,226,449) or (4) a method wherein free radicals are generated by heat (U.S. Pat. No. 3,404,189 or JP-B-95-59525) has, for example, been reported.

However, a distillation column is usually an apparatus for separating a desired compound and has not been intended for carrying out a reaction.

Further, the reaction selectivity in the above method (1) is governed by the ratio of the alkanol and $R^FCH=CH_2$ to the total amount of feed. But the method has had a drawback that when the concentration of the polyfluoroalkyl alcohol increases as the reaction progresses, the product $R^F(CH_2)_2 CH(R^{10})$—OH undergoes a side reaction with $R^FCH=CH_2$ to lower the selectivity.

The method (2) also has had a drawback that like in the method (1), the reaction rate of a side reaction increases as the reaction progresses, whereby the selectivity deteriorates.

Further, both methods (1) and (2) have had a problem that the volume efficiency decreases if the proportion of the alkanol is increased to maintain high selectivity, and they are disadvantageous as industrial processes.

The methods (3) and (4) have had a problem that there is a distribution in the number of polymerized units of tetrafluoroethylene introduced by the telomerization, so that the chain length distribution of per fluoroalkyl groups in the product tends to be broad. In order to selectively obtain a perfluoroalkyl iodide having a desired chain length, a method has been proposed in which a feedstock having a low carbon number is used in a large amount, and the reaction is carried out at a low conversion. However, a large amount of the feedstock has to be circulated, and there is a problem that the production efficiency is low.

The present inventors have conducted a study for a production method with high efficiency at high selectivity and as a result, have found the method of the present invention which solves the above problems and which is excellent in mass production. Further, the production method has been found to be applicable to the production of other compounds. The present invention has been accomplished on the basis of these discoveries.

Thus, the present invention provides a production method which comprises reacting one or more feedstock compounds to form a desired compound having a boiling point higher than the feedstock compounds, wherein the reaction is carried out under reflux in a distillation column portion of a reactor provided with the distillation column.

Now, the present invention will be described in detail with reference to the preferred embodiments.

In the present invention, the feedstock compounds are compounds essential as feedstocks for the reaction of the present invention. Such feedstock compounds may be used alone or in combination as a mixture of two or more of them. From the viewpoint of the distribution in the distillation column, one or two types of compounds are preferred.

In the present invention, the desired compound is a compound which is obtained by the reaction of the feedstock compounds and a product having a boiling point higher than any one of the feedstock compounds. The desired compound may be one or more types, preferably one type. The difference in boiling point between the desired compound and the feedstock compounds is preferably at least 5° C., more preferably from 40 to 200° C. If the difference in boiling point is small, separation by distillation in the distillation column tends to be difficult, and there will be a drawback that the desired compound can not efficiently be obtained.

In the production method of the present invention, a reactor provided with a distillation column is employed. In the present invention, the reactor is not meant only for an apparatus wherein the reaction is actually takes place, but it is meant for the entire apparatus relating to the reaction of the present invention. As such a reactor, a reactor comprising a still portion, a distillation column portion and a condenser portion, is preferred. Namely, a common reactor called a distillation column type reactor is preferred. The distillation column may be of any type so long as it is capable of separating the desired compound and the feedstock compounds by distillation. For example, a plate column or a packed column is preferred. The still portion may, for example, be of a vessel type, a tubular type or a tower type. Further, the reactor may be a plate column type reactor having the still portion and the distillation column portion unified or integrated.

In the present invention, the reaction is carried out in the distillation column portion under reflux. Accordingly, the reaction for the production method of the present invention is a reaction which proceeds under reflux in a distillation column.

In the production method of the present invention, compounds other than the feedstock compounds and the desired compound, may be present in the distillation column portion. Such other compounds may, for example, be compounds which are used for the purpose of efficiently carrying out the reaction, such as a reaction accelerator or a reaction auxiliary material, although they are not essential to the reaction of the present invention. Such other compounds may be preliminarily present in the distillation column, or may continuously be introduced into the distillation column.

As such other compounds, compounds which are azeotropically distillable together with the feedstock compounds, or compounds having boiling points lower than the reflux temperature, are preferred. Such other compounds may adversely affect the reaction if they are present in the reaction system for a long period of time, and it is advisable to take into consideration their half-lives under the reaction conditions.

When the feedstock compounds (and other compounds, as the case requires) are continuously supplied, the feeding amount is adjusted to the reaction rate, so that the reaction can be carried out at high selectivity. Further, the feeding position to the distillation column for the continuous feeding is preferably at an upper to middle portion of the distillation column, more preferably at a portion above ½ of the distillation column, particularly preferably at a portion from the top to ⅔ from the top of the distillation column. Such a feeding position is preferably a position where the concentration of the desired compound in the distillation column is low, particularly preferably a position where the desired compound is not refluxed.

Here, the upper portion of the distillation column is meant for a portion from the top to less than ⅓ from the top, when the distillation column portion is equally divided into three. Accordingly, the middle portion of the distillation column is meant for a portion corresponding to from ⅓ to ⅔ from the top, and the lower portion of the distillation column is meant for a portion corresponding to more than ⅔ from the top to the bottom of the distillation column portion. In a case where the reactor is a plate column type reactor, the lowest portion of the distillation column is meant for the liquid surface of the reaction product containing the desired compound in the vicinity of the lower portion of the plate column type reactor.

The desired compound produced by the production method of the present invention has a boiling point higher than the feedstock compounds, and it naturally descends towards the lower portion of the distillation column. The desired compound moved to the lower portion of the distillation column may be continuously withdrawn or intermittently withdrawn (in a batch system). The feedstock compounds may be supplied continuously or intermittently. When the desired compound is withdrawn continuously, it is preferred to continuously supply the feedstock compounds.

When the feedstock compounds are continuously supplied, it is preferred to supply them to the distillation column portion. If the feedstock compounds are deficient in the reaction site, there will be a drawback that the conversion decreases. Further, at the start of the reaction, one or more feedstock compounds may preliminarily be refluxed in the distillation column portion.

In the production method of the present invention, the desired compound formed in the distillation column naturally moves towards the lower portion of the distillation column. Accordingly, the concentration of the desired compound in the distillation column at the reaction site becomes low. Therefor, the distillation column type production method of the present invention is particularly effective when applied to such a reaction that the desired compound should not be present at the reaction site.

A reaction to which the production method of the present invention can be preferably applied, may, for example, be a reaction (hereinafter referred to as reaction A) wherein the desired compound undergoes a side reaction with the feedstock compounds, or a reaction (hereinafter referred to as reaction B) wherein a plurality of reaction sites are present in the feedstock compounds and it is desired to carry out the reaction only at a certain specific reaction site among such reaction sites.

Reaction A may, for example, be a reaction (hereinafter referred to as reaction $A^1$) for producing the after-mentioned fluorine-containing hydroxy compound (3), a method (hereinafter referred to as reaction $A^2$) for producing the after-mentioned $C_nF_{2n+1}(CF_2CF_2)_mI$ (wherein n is an integer of from 2 to 12, m is an integer of from 1 to 6, and $4 \leq n+2m \leq 14$) by telomerization, or a reaction for producing $R^FCH_2CH_2OR^3$ (wherein $R^f$ is a monovalent fluorine-containing organic group having from 1 to 20 carbon atoms, and $R^3$ is an alkyl group) by adding $R^3OH$ or $R^3OM$ (wherein M is an alkali metal) to $R^fCH=CH_2$.

Reaction B may, for example, be a case wherein a feedstock compound having a symmetrical structure and having the same reactive groups at both ends of the molecule, is reacted with another feedstock compound so that the latter compound is reacted only to the reactive group at one end.

Among these reactions, the production method of the present invention is preferably applied to the above reaction A, particularly reaction $A^1$ or $A^2$.

Now, reaction $A^1$ will be described. Reaction $A^1$ is a production method which comprises reacting a fluorine-containing unsaturated compound (1) and a hydroxyl compound (2) in the presence of a free radical initiator to obtain a fluorine-containing hydroxyl compound (3), wherein the reaction is carried out under reflux in a distillation column portion of a reactor provided with the distillation column:

$$R^f\text{—}Q\text{—}CH=CH_2 \quad (1)$$

$$CHR^1R^2\text{—}OH \quad (2)$$

$$R^f\text{—}Q\text{—}CH_2CH_2CR^1R^2OH \quad (3)$$

wherein $R^f$ is a monovalent fluorine-containing organic group having from 1 to 20 carbon atoms, Q is a single bond or a bivalent linking group, and each of $R^1$ and $R^2$ which are independent of each other, is a hydrogen atom or an alkyl group having from 1 to 5 carbon atoms, provided that the sum of the carbon numbers in $R^1$ and $R^2$ is from 0 to 5.

$R^f$ in the fluorine-containing unsaturated compound (1) is a monovalent fluorine-containing organic group having from 1 to 20 carbon atoms. In this specification, "fluorine-containing organic group" means an organic group containing at least one fluorine atom. The monovalent fluorine-containing organic group is preferably "a monovalent fluorine-containing hydrocarbon group" which is a group having at least one of hydrogen atoms of a monovalent hydrocarbon group substituted by a fluorine atom.

The monovalent fluorine-containing hydrocarbon group may be "a monovalent fluorine-containing aromatic hydrocarbon group" having at least one of hydrogen atoms of a monovalent aromatic hydrocarbon group substituted by a fluorine atom or "a monovalent fluorine-containing aliphatic hydrocarbon group" having at least one of hydrogen atoms of a monovalent aliphatic hydrocarbon group substituted by a fluorine atom. A monovalent fluorine-containing aliphatic hydrocarbon group is preferred. The carbon number of the monovalent fluorine-containing aliphatic hydrocarbon group is preferably from 1 to 18, more preferably from 1 to 12, particularly preferably from 2 to 12. Further, the monovalent fluorine-containing aromatic hydrocarbon group may have at lest one of hydrogen atoms substituted by a monovalent hydrocarbon group such as an alkyl group. The carbon number of the monovalent fluorine-containing aromatic hydrocarbon group is preferably from 6 to 12, more preferably from 6 to 8.

Further, the monovalent fluorine-containing hydrocarbon group of the present invention may have at least one ether-type oxygen atom or a thioether-type sulfur atom inserted between carbon atoms of a carbon-carbon bond of the above monovalent fluorine-containing aliphatic hydrocarbon group.

When $R^f$ is a monovalent fluorine-containing aliphatic hydrocarbon group, it is preferably "a fluorine-containing alkyl group" having at least one of hydrogen atoms of an alkyl group substituted by a fluorine atom, particularly preferably "a polyfluoroalkyl group" having at least two hydrogen atoms of an alkyl group substituted by fluorine atoms. Further, it is preferred that from 1 to 3 fluorine atoms are bonded to the terminal carbon bonded to Q of the monovalent fluorine-containing aliphatic hydrocarbon group. The carbon number of the polyfluoroalkyl group is preferably from 1 to 20, more preferably from 1 to 15, particularly preferably from 6 to 12. Further, such a polyfluoroalkyl group may have at least one ether-type oxygen atom or a thioether-type sulfur atom inserted between carbon atoms of a carbon-carbon bond of the alkyl group.

When $R^f$ is a polyfluoroalkyl group, the proportion of fluorine atoms in the polyfluoroalkyl group i.e. [(number of fluorine atoms in the polyfluoroalkyl group)/(number of hydrogen atoms of an alkyl group having the same carbon number as the polyfluoroalkyl group)]×100 (%), is preferably at least 60%, more preferably at least 80%, particularly preferably substantially 100% i.e. a perfluoroalkyl group.

The polyfluoroalkyl group may have a straight chain structure or a branched chain structure, preferably a straight chain structure. In the case of a branched chain structure, the branched moiety is preferably a short chain having from 1 to 3 carbon atoms. Further, the polyfluoroalkyl group may have hydrogen atoms at the terminal.

When $R^f$ is a monovalent fluorine-containing aromatic hydrocarbon group, it is preferably a group having at least one hydrogen atom in an aryl group such as a phenyl group, an aralkyl group such as a benzyl group or a group having a lower alkyl group substituted on such an aryl or aralkyl group substituted by a fluorine atom.

Specific examples of $R^f$ include those having the following structures, but $R^f$ is not limited to such specific examples. The following examples include "structure-isomeric groups" which are groups having the same molecular formulae but different structures.

$C_2F_5$—, $C_3F_7$— (inducing both $CF_3(CF_2)_2$— and $(CF_3)_2CF$—), $C_4F_9$— (including $CF_3(CF_2)_3$—, $(CF_3)_2CFCF_2$—, $(CF_3)_3C$— and $CF_3CF_2CF(CF_3)$—), $C_5F_{11}$— (including structure-isomeric groups such as $CF_3(CF_2)_4$—, $(CF_3)_2CF(CF_2)_2$—, $(CF_3)_3CCF_2$— and $CF_3CF_2CF(CF_3)CF_2$—), $C_6F_{13}$— (including structure-isomeric groups such as $CF_3(CF_2)_2C(CF_3)_2$—, $C_8F_{17}$—, $C_{10}F_{21}$—, $C_{12}F_{25}$—, $C_{15}F_{31}$—, $HC_tF_{2t}$— (t=an integer of from 1 to 20), $(CF_3)_2CFC_sF_{2s}$— (s=an integer of from 1 to 17), $CF_3(CF_2)_4OCF(CF_3)$—, $F[CF(CF_3)CF_2O]_sCF(CF_3)CF_2CF_2$—, $F[CF(CF_3)CF_2O]_tCF(CF_3)$—, $F[CF(CF_3)CF_2O]_uCF_2CF_2$—, $F(CF_2CF_2CF_2O)_vCF_2CF_2$—, $F(CF_2CF_2O)_wCF_2CF_2$—, $C_6F_5$— (s=an integer of from 1 to 5, t=an integer of from 1 to 6, u=an integer of from 2 to 6, v=an integer of from 1 to 6, and w=an integer of from 1 to 9).

Q in the fluorine-containing unsaturated compound (1) is a single bond or a bivalent organic group, preferably a single bond. When Q is a single bond, $R^f$ and $CH=CH_2$ in the formula (1) are directly bonded to each other, and likewise, in the formula (3), $R^f$ and $CH_2$—$CH_2$—$CR^1R^2$—$OH$ are directly bonded to each other.

When Q is a bivalent organic group, Q preferably contains no fluorine atom. Q is preferably a bivalent hydrocarbon group having from 1 to 8 carbon atoms, or a bivalent hydrocarbon group containing atoms inert to the reaction of the present invention. Specifically, Q is preferably a $C_{1-8}$ alkylene group, particularly preferably a $C_{1-5}$ alkylene group. Such an alkylene group may be a straight chain alkylene group or a branched alkylene group. Preferred is a straight chain alkylene group. In the case of a branched alkylene group, the branched moiety is preferably a short chain having from about 1 to 3 carbon atoms. Q is preferably a single bond or a methylene group.

In a case where Q is a bivalent hydrocarbon group having inert carbon atoms, it may, for example, be a bivalent hydrocarbon group containing an ether-type oxygen atom, a thioether-type sulfur atom or a nitrogen atom to which no hydrogen atom is bonded. For example, —$(CH_2)_2O(CH_2)_3$—, —$CH_2O(CH_2)_3$—, —$(CH_2)_2S(CH_2)_3$— or —$SO_2NR$— (wherein R is a $C_{1-3}$ alkyl group) may be mentioned.

The fluorine-containing unsaturated compound (1) includes the following specific examples.

$CF_3CF_2CH=CH_2$,
$CF_3(CF_2)_2CH=CH_2$,
$CF_3(CF_2)_3CH=CH_2$,
$CF_3(CF_2)_4CH=CH_2$,
$CF_3(CF_2)_5CH=CH_2$,
$CF_3(CF_2)_7CH=CH_2$,
$CF_3(CF_2)_9CH=CH_2$,
$CF_3(CF_2)_{11}CH=CH_2$,
$H(CF_2)_4CH=CH_2$,
$H(CF_2)_6CH=CH_2$,
$H(CF_2)_8CH=CH_2$,
$H(CF_2)_{10}CH=CH_2$,
$H(CF_2)_{12}CH=CH_2$,
$CF_3CF_2CH_2CH=CH_2$,
$CF_3(CF_2)_2CH_2CH=CH_2$,
$CF_3(CF_2)_3CH_2CH=CH_2$,
$CF_3(CF_2)_4CH_2CH=CH_2$,
$CF_3(CF_2)_5CH_2CH=CH_2$,
$CF_3(CF_2)_7CH_2CH=CH_2$,
$CF_3(CF_2)_9CH_2CH=CH_2$,
$CF_3(CF_2)_{11}CH_2CH=CH_2$,
$H(CF_2)_4CH_2CH=CH_2$,
$H(CF_2)_6CH_2CH=CH_2$,
$H(CF_2)_8CH_2CH=CH_2$,
$H(CF_2)_{10}CH_2CH=CH_2$,
$H(CF_2)_{12}CH_2CH=CH_2$,
$(CF_3)_2CF(CF_2)_2CH=CH_2$,
$(CF_3)_2CF(CF_2)_4CH=CH_2$,
$(CF_3)_2CF(CF_2)_6CH=CH_2$,
$(CF_3)_2CF(CF_2)_8CH=CH_2$,
$(CF_3)_2CF(CF_2)_{10}CH=CH_2$,
$(CF_3)_2CF(CF_2)_{12}CH=CH_2$.
$(CF_3)_2CF(CF_2)_2CH_2CH=CH_2$,
$(CF_3)_2CF(CF_2)_4CH_2CH=CH_2$,
$(CF_3)_2CF(CF_2)_6CH_2CH=CH_2$,
$(CF_3)_2CF(CF_2)_8CH_2CH=CH_2$,
$(CF_3)_2CF(CF_2)_{10}CH_2CH=CH_2$,
$(CF_3)_2CF(CF_2)_{12}CH_2CH=CH_2$.

Such fluorine-containing unsaturated compounds (1) are known compounds. The fluorine-containing unsaturated compounds (1) may be used alone or in combination as a mixture of two or more of them, preferably alone. If two or more of them are used in combination, they are preferably those having different $R^f$ groups or those having $R^f$ groups having different carbon numbers. Such a combination may be suitably adjusted depending upon the composition of the fluorine-containing unsaturated compound (1) and the particular purpose of the product.

Each of $R^1$ and $R^2$ in the hydroxyl compound (2) is a hydrogen atom or an alkyl group having from 1 to 5 carbon atoms, provided that the sum of carbon numbers in $R^1$ and $R^2$ is from 0 to 5.

The hydroxyl compound (2) is preferably methanol, ethanol, n-propanol, isopropanol, n-butanol, isobutanol, 2-butanol, 3-methyl-2-butanol, n-pentanol, 2-pentanol, 3-pentanol, 4-methyl-2-pentanol, neopentyl alcohol, isoamyl alcohol, 2-methyl-1-butanol, 2-ethyl-1-butanol, 2-methyl-1-pentanol, or n-hexanol, particularly preferably methanol, ethanol or isopropanol. The hydroxyl compound (2) may have a straight chain or branched structure.

The hydroxyl compound (2) may be continuously supplied to the reactor or may preliminarily be introduced into the reactor. When the desired compound is continuously withdrawn, the continuous supply is preferred.

The fluorine-containing unsaturated compound (1) is reacted with the hydroxyl compound (2) in the presence of a free radical initiator. The free radical initiator may be an inorganic compound or an organic compound, preferably an organic compound. It may, for example, be a peroxy organic compound or an azo organic compound, which is commonly used as a radical-forming agent. A peroxy organic compound is preferred.

Further, as the free radical initiator, an organic compound having a boiling point not higher than the reaction temperature is preferred. The organic compound having such a boiling point is effective for preventing the side reaction of the product at the lower portion of the reactor. Further, the free radical initiator is preferably selected from an organic compound azeotropically distillable together with the fluorine-containing unsaturated compound (1) and/or the hydroxyl compound (2), and an organic compound having a half-life of at most 10 minutes at the reaction temperature.

Further, as the free radical initiator, a peroxy organic compound is preferred, which may, for example, be an alkylhydroperoxy compound, a dialkylperoxy compound, a peroxy ketal, a diacylperoxy compound, a peroxy carboxylic acid ester, a peroxy carboxylic acid or a peroxy carbonate. More specifically, it may, for example, be 1,1-bis(t-butylperoxy)-3,3,5-trimethylcyclohexane, 1,1-bis(t-butylperoxy)cyclohexane, t-butylperoxyisopropyl carbonate, t-butylperoxyisobutylate, t-butylperoxypivalate, di-t-butylperoxide or t-butylhydroxyperoxide.

Further, the free radical initiator may particularly preferably be di-t-butylperoxide azeotropically distillable with methanol, or t-butylperoxyisopropyl carbonate having a half-life of at most 10 minutes at 150° C.

The free radical initiator may preliminarily be introduced into the reactor. However, in a case where the fluorine-containing unsaturated compound (1) is supplied over a long period of time or in a case where the desired compound is continuously withdrawn, it is preferred to continuously supply it. On the other hand, in a case where the fluorine-containing unsaturated compound (1) is supplied in a short period of time or in a case where the desired compound is withdrawn intermittently (a batch system), the free radical initiator and the hydroxyl compound (2) may be continuously supplied or preliminarily introduced. The compound introduced in the distillation column is preferably refluxed.

When the respective materials are supplied continuously, the proportions of the fluorine-containing unsaturated compound (1), the hydroxyl compound (2) and the free radical initiator are preferably such that per mol of the fluorine-containing unsaturated compound (1), the hydroxyl compound (2) is from 1 to 100 mol, more preferably from 1 to 20 mol, and the free radical initiator is from 0.002 to 5 mol, more preferably from 0.01 to 0.2 mol. In a case where a reaction inhibitor is formed by a side reaction from e.g. the free radical initiator, a part of the reflux may be withdrawn continuously or intermittently out of the system.

The reaction time for reaction $A^1$ is preferably from 1 to 360 minutes, more preferably from 1 to 20 minutes. The reaction temperature may suitably be adjusted depending upon the structures of the feedstock compounds, etc. It is usually preferably within a range of from 90 to 160° C., more preferably from 100 to 130° C. The reaction temperature is represented by the temperature at the reaction site in the distillation column, and in a case where the fluorine-containing unsaturated compound (1) is continuously supplied, the reaction temperature is preferably the temperature at the feeding position in the distillation column. At a portion in the distillation column lower than such a position, the temperature becomes higher. The reaction pressure is preferably from 0 to 20 kg/cm$^2$ (gauge pressure), more preferably from 1 to 10 kg/cm$^2$ (gauge pressure).

The fluorine-containing unsaturated compound (1) and the hydroxyl compound (2) have lower boiling points than the fluorine-containing hydroxyl compound (3). Accordingly, when a reactor provided with a distillation column is used, and refluxing takes place at the same time as the reaction takes place at the distillation column portion, the desired compound moves downwardly in the reactor, and the concentration of the desired compound becomes low at the reaction site. Further, in a case where the feedstock compounds are continuously supplied in correspondence with the reaction rate, the reaction can be carried out constantly at high selectivity. Further, as the concentration of the fluorine-containing unsaturated compound (1) becomes low at the reaction site, it is possible to prevent the side reaction of the fluorine-containing hydroxyl compound (3) with the fluorine-containing unsaturated compound (1).

In reaction $A^1$, the hydroxyl compound (2) is radically added to the double bond of the fluorine-containing unsaturated compound (1) to form the fluorine-containing hydroxyl compound (3). Specific examples of the fluorine-containing hydroxyl compound (3) include the following compounds, wherein $R^f$ is the above mentioned polyfluoroalkyl group, preferably a perfluoroalkyl group.

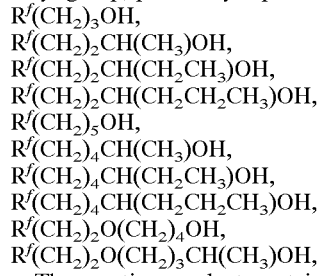

$R^f(CH_2)_3OH$,
$R^f(CH_2)_2CH(CH_3)OH$,
$R^f(CH_2)_2CH(CH_2CH_3)OH$,
$R^f(CH_2)_2CH(CH_2CH_2CH_3)OH$,
$R^f(CH_2)_5OH$,
$R^f(CH_2)_4CH(CH_3)OH$,
$R^f(CH_2)_4CH(CH_2CH_3)OH$,
$R^f(CH_2)_4CH(CH_2CH_2CH_3)OH$,
$R^f(CH_2)_2O(CH_2)_4OH$,
$R^f(CH_2)_2O(CH_2)_3CH(CH_3)OH$,

The reaction product containing the fluorine-containing hydroxyl compound (3) which is the desired compound of the reaction $A^1$, may be withdrawn continuously or intermittently from the lower portion of the reactor. When it is withdrawn continuously, it is preferred and effective to supply feedstock compounds at a rate such that the residence time of the desired compound will be from 1 to 360 minutes. The residence time can be calculated from the amount of the feedstock compounds supplied.

The reaction product containing the fluorine-containing hydroxyl compound (3) may be subjected to purification treatment as the case requires to obtain a highly pure fluorine-containing hydroxyl compound (3). The fluorine-containing hydroxyl compound (3) is a compound useful as a water and oil repellent, a surfactant, a release agent or an intermediate for pharmaceuticals or agricultural chemicals.

Now, reaction $A^2$ will be described. Reaction $A^2$ is a method for producing a perfluoroalkyl iodide, which comprises telomerizing m mol of tetrafluoroethylene to 1 mol of a telogen (4) in the presence of a free radical initiator to obtain a perfluoroalkyl iodide (5), wherein a reactor provided with a distillation column is used, and the telomerization is carried out in the distillation column in which the telogen is refluxed.

$$C_nF_{2n+1}I \qquad (4)$$

$$C_nF_{2n+1}(CF_2CF_2)_mI \qquad (5)$$

wherein n is an integer of from 2 to 12, and m is an integer of from 1 to 6, provided that $4 \leq n+2m \leq 14$.

In the telogen (4), n is preferably 2 or 3. The telogen (4) wherein n is 2 or 3 is preferably perfluoroethyl iodide ($CF_2CF_2I$) or a perfluoroisopropyl iodide ($(CF_3)_2CFI$).

Further, if n is 4 or more, it is preferred to employ the one wherein the $C_nF_{2n+1}$— moiety is a straight chain, or the one in which the terminal portion remote from iodine is a perfluoroisopropyl group ($(CF_3)_2CF$—).

The telogen wherein n is at least 4 and the terminal is a perfluoroethyl or perfluoroisopropyl group, is preferred, since it is a compound obtainable by telomerizing tetrafluoroethylene $CF_2=CF_2$ (hereinafter referred to as TFE) to perfluoroethyl iodide or perfluoroisopropyl iodide, as described hereinafter. Specific examples of the telogen (4) include the following compounds.

$CF_3(CF_2)_3I$,
$CF_3(CF_2)_5I$,
$CF_3(CF_2)_7I$,
$CF_3(CF_2)_9I$,
$CF_3(CF_2)_{11}I$,
$(CF_3)_2CF(CF_2)_2I$,
$(CF_3)_2CF(CF_2)_4I$,
$(CF_3)_2CF(CF_2)_6I$,
$(CF_3)_2CF(CF_2)_8I$.

In reaction $A^2$, m mol of TFE is telomerized to 1 mol of the telogen (4) to obtain the perfluoroalkyl iodide (5).

The $C_nF_{2n+1}$— moiety in the formula (5) has the same structure as the corresponding moiety in the formula (4). For example, when $(CF_3)_2CFI$ is used as the telogen, the structure of the $C_nF_{2n+1}$— moiety in the formula (5) will be $(CF_3)_2CF$—.

Further, m is an integer of from 1 to 6. When 1 mol of TFE is telomerized to 1 mol of the telogen, m in the formula (5) is 1, and m is preferably 1. In a case where a product wherein m is 2 or more, is desired, it is preferred to repeat the reaction in a plurality of times, so that the molecular weight distribution of the product can thereby be made narrow.

In a usual case, the molar amount of TFE telomerized to the telogen in the telomerization reaction is not uniform, and the product will accordingly be a mixture of perfluoroalkyl iodides (5) wherein the numbers of m are different. The amount of TFE to be telomerized may vary depending upon the amount of TFE used or the degree of the progress of the telomerization reaction.

The amount of TFE to the telogen may suitably be adjusted depending upon the chain length of the desired product, etc. It is preferred to employ from 0.1 to 0.8 molar time of TFE relative to the theoretical molar amount required for the desired chain length. In this way, it is possible to obtain a perfluoroalkyl iodide having a narrow distribution of m.

The carbon number of the perfluoroalkyl iodide (5) is from 4 to 14, i.e. $4 \leq n-2m \leq 14$. If the carbon number of the perfluoroalkyl iodide exceeds 14, there will be a problem that the boiling point tends to be very high.

The telomerization reaction is carried out in the presence of the free radical initiator. The free radical initiator may be a known or well known free radical initiator, and it may be a free radical initiator made of an inorganic compound or a free radical initiator made of an organic compound, preferably a free radical initiator made of an organic compound.

As the free radical initiator, a compound volatile at the reaction temperature is preferred, since it can efficiently be present in the reaction system, and it is advantageous also from the viewpoint of post treatment. Particularly preferred is a free radical initiator which is azeotropically distillable together with the perfluoroalkyl iodide.

The free radical initiator in reaction $A^2$ may, for example, be a ketone peroxy compound, a peroxy ketal compound, a hydroperoxide compound, a dialkylperoxide compound, a diacylperoxy compound, a peroxy dicarbonate, a peroxyester compound or an azo compound, preferably diisopropylperoxy dicarbonate or isobutylylperoxide. The amount of the free radical initiator is preferably from 0.002 to 0.2 mol per mol of TFE.

The telomerization reaction is carried out in a distillation column wherein the telogen is refluxed. The telomerization reaction is carried out by using a reactor provided with a distillation column and in the distillation column wherein the telogen is refluxed. It is preferred to carry out the reaction while continuously supplying TFE. The telogen and/or the free radical initiator may be preliminarily present in the reactor or may be continuously supplied.

The reaction temperature for the telomerization reaction is preferably lower than the boiling point of the perfluoroalkyl iodide under the pressure in the distillation column. Further, the reaction temperature is preferably a temperature at which the half-life time of the free radical initiator is not more than one hour, more preferably not more than 10 minutes, particularly not more than 5 minutes. Usually, the reaction temperature is from 70 to 180° C. This reaction temperature is a temperature at the portion in the distillation column where the telomerization reaction takes place. In a case where TFE is continuously supplied, it is preferably the temperature measured at the portion of the distillation column to which TFE is introduced. The temperature at a portion located below such a portion in the reactor, becomes higher.

The reaction pressure varies depending upon the reaction temperature and preferably at a level higher by from 0 to 5 $kg/cm^2$ (gauge pressure) than the vapor pressure of the telogen at the reaction temperature. If the reaction pressure is too high, the selectivity of the reaction tends to deteriorate.

When TFE is continuously supplied, the feeding position is preferably at a height in the vicinity of one half of the distillation column. When the telogen is also continuously supplied, it is preferably supplied at a position higher than the feeding position of TFE, and it is preferably supplied in the vicinity of the upper portion of the distillation column. The feeding rate of the telogen is preferably as close as possible to the reaction rate. By adjusting the feeding amount to the reaction rate, the reaction can be carried out constantly at high selectivity. Further, in a case where the telogen is continuously supplied to obtain a product wherein m is 1, the total amount of the telogen supplied is preferably at a level equimolar to TFE.

In reaction $A^2$, the free radical initiator is also preferably continuously supplied. The free radical initiator is preferably supplied to the distillation column portion, particularly from a higher position of the distillation column portion. It is particularly preferred to introduce it from a portion above ½ height of the distillation column. More preferably, it is introduced from the top of the distillation column. Further, the free radical initiator may be supplied as diluted by the telogen or by a high boiling point solvent inert to the reaction.

In a case where the telogen, TFE and the free radical initiator are all continuously supplied, the amount of TFE is preferably from 0.01 to 5 mol per mol of the telogen, and the free radical initiator is supplied preferably in an amount of from $2 \times 10^{-6}$ to 1 mol per mol of the telogen.

Further, when TFE is supplied continuously, or when the telogen and/or the free radical initiator is continuously supplied together with TFE, it is preferred to adjust the feeding rate of TFE so that the residence time will be from 1 to 360 minutes.

It is desired to heat the lower portion of the reactor sufficiently, so that adequate refluxing takes place in the distillation column to such an extent that separation of the telogen and the perfluoroalkyl iodide by distillation is possible.

The perfluoroalkyl iodide formed by reaction $A^2$ moves downwards in the reactor due to the difference in the vapor pressure from the telogen or TFE. The telogen and TFE in reaction $A^2$ have boiling points lower than the reaction product. Accordingly, when the reaction is carried out by means of a reactor provided with a distillation column, and refluxing is carried out simultaneously, the high boiling point reaction product moves downwardly in the reactor, whereby the concentration of the reaction product at the reaction site can be lowered.

The reaction product containing the perfluoroalkyl iodide may be continuously or intermittently withdrawn, which is preferred as the productivity is thereby improved. Further, the reaction product is preferably purified to have a high purity. If a reaction inhibitor is produced by a side reaction from e.g. the free radical initiator in the distillation column, a part of the reflux may be withdrawn continuously or intermittently.

Specific examples of the perfluoroalkyl iodide as the desired compound in reaction $A^2$ include the following compounds.

$CF_3(CF_2)_3I$,
$CF_3(CF_2)_5I$,
$CF_3(CF_2)_7I$,
$CF_3(CF_2)_9I$,
$CF_3(CF_2)_{11}I$,
$CF_3(CF_2)_{13}I$,
$CF_3(CF_2)_{15}I$,
$CF_3(CF_2)_{17}I$,
$(CF_3)_2CF(CF_2)_2I$,
$(CF_3)_2CF(CF_2)_4I$,
$(CF_3)_2CF(CF_2)_6I$,
$(CF_3)_2CF(CF_2)_8I$,
$(CF_3)_2CF(CF_2)_{10}I$,
$(CF_3)_2CF(CF_2)_{12}I$,
$(CF_3)_2CF(CF_2)_{14}I$.

The perfluoroalkyl iodide (5) is a compound useful as a monomer for a various resins, a fluoroalkyl silicon material, a water and oil repellent material, a surfactant material, a functional material or an intermediate for pharmaceuticals or agricultural chemicals.

According to the distillation column type production method of the present invention, the desired compound can be produced highly selectively and highly efficiently. The production method of the present invention is a method which can be carried out without using special conditions or reagents, and it is a highly practical method which can be used as an industrial production method of a large capacity.

Now, the present invention will be described in further detail with reference to Examples. However, it should be understood that the present invention is by no means restricted to such specific Examples.

EXAMPLE 1

A packing material for separation by distillation was packed into a distillation column (inner diameter: 40 mm, length: 650 mm) having a reflux condenser at the top, and a feeding inlet was provided at a position corresponding to ⅓ from the top of the distillation column. Further, a stainless steel double tube (inner diameter: about 70 mm, length: about 210 mm) with the space between the double tube constituting a jacket (internal capacity: about 800 ml) was connected as a still portion to the lowest portion of the distillation column to form a reactor.

To the still portion, methanol (450 g) and di-t-butyl peroxide (7.4 g) were charged, and a heating medium was circulated into the jacket to raise the internal temperature to 130° C. and to reflux an azeotropic mixture of methanol and di-t-butyl peroxide (azeotropic composition: methanol/di-t-butyl peroxide=59/41), whereupon $CF_3CF_2CH=CH_2$ (150 g) was continuously supplied from the feeding inlet at 0.417 g/min for 6 hours. The temperature of the distillation portion at that time was within a range of from 127 to 131° C., and the pressure in the reactor was about 9 kg/cm² (gauge pressure).

Six hours later, the feeding was stopped and the temperature was lowered, whereupon the reaction product containing $CF_3CF_2CH_2CH_2CH_2OH$ remaining in the still at the lower portion of the reactor, was withdrawn and quantitatively analyzed by gas chromatography (GC), whereby the conversion was 99% based on $CF_3CF_2CH=CH_2$, and the selectivity for $CF_3CF_2CH_2CH_2CH_2OH$ was 97%.

EXAMPLE 2

Into the same stainless steel tubular reactor as used in Example 1, 458 g of $CF_3(CF_2)_7CH=CH_2$ was introduced instead of $CF_3CF_2CH=CH_2$, and the reaction was carried out in the same manner. Six hours later, the feeding was stopped, and the temperature was lowered, whereupon the reaction product containing $CF_3(CF_2)_7CH_2CH_2CH_2OH$ remaining in the reactor, was withdrawn and quantitatively analyzed by GC, whereby the conversion was 99% based on $CF_3(CF_2)_7CH=CH_2$, and the selectivity for $CF_3(CF_2)_7CH_2CH_2CH_2OH$ was 95%.

EXAMPLE 3

The reaction was carried out in the same manner as in Example 1, and then from the feeding inlet at the position corresponding to ⅓ from the top of the distillation column, 0.1 g/min of methanol, 0.02 g/min of di-t-butyl peroxide and 0.417 g/min of $CF_3CF_2CH=CH_2$ were continuously supplied, and at the same time from the still portion, the product was withdrawn at a rate of 0.5 g/min. The liquid withdrawn was analyzed by GC, whereby the conversion was 99%, and the selectivity was 97%.

COMPARATIVE EXAMPLE 1

Into an autoclave having an internal capacity of 1000 ml and equipped with a stirrer, methanol (450 g) and di-t-butyl peroxide (7.4 g) were charged, and the internal temperature was raised to 130° C., whereupon the $CF_3CF_2CH=CH_2$ (150 g) was continuously supplied at a rate of 0.417 g/min for 5 hours. The maximum pressure in the reactor was 8.8 kg/cm² (gauge pressure). After termination of the feeding, aging was carried out for 2 hours, whereupon the temperature was lowered, and the reaction solution was withdrawn and quantitatively analyzed by GC, whereby the conversion was 90% based on $CF_3CF_2CH=CH_2$, and the selectivity for $CF_3CF_2CH_2CH_2CH_2OH$ was 75%.

EXAMPLE 4

A packing material for separation by distillation was packed into a distillation column (inner diameter: 40 mm, length: 650 mm) having a reflux condenser at the top, and a feeding inlet was provided at a position corresponding to 150 mm from the top of the distillation column. Further, a stainless steel double tube (inner diameter: about 70 mm, length: about 210 mm) with the space between the double tube constituting a jacket (internal capacity: about 800 ml) was connected as a still portion to the lowest portion of the distillation column to form a reactor.

To the still portion, 738 g of perfluoroethyl iodide was charged, and a heating medium was circulated into the jacket to raise the temperature until the temperature at the feeding inlet portion of the distillation column became 75° C. The pressure at that time was 6 kg/cm² (gauge pressure). From the top of the distillation column, a 2 wt % perfluoroethyl iodide solution of diisopropyl peroxy dicarbonate and from the middle portion, TFE, were supplied at rates of 25.75 g/hr and 25.0 g/hr, respectively. At that time, the temperature at the feeding inlet portion of the distillation column was maintained at 75° C.

Upon expiration of 30 minutes from termination of the feeding, the reactor was cooled, and the liquid remaining in the reactor was withdrawn and quantitatively analyzed (unit: area %) by GC. As perfluoroalkyl iodides other than unreacted $CF_3CF_2I$, 71% of $CF_3(CF_2)_3I$, 20% of $CF_3(CF_2)_5I$ and 9% of $CF_3(CF_2)_7I$ were detected.

COMPARATIVE EXAMPLE 2

Into an autoclave having an internal capacity of 1000 ml and equipped with a stirrer, 738 g of perfluoroethyl iodide was charged. After raising the internal temperature of the reactor to 75° C., a 2 wt % perfluoroethyl iodide solution of diisopropyl peroxy dicarbonate and TFE were supplied at rates of 25.75 g/hr and 25.0 g/hr, respectively, for 4 hours.

After aging for 30 minutes from termination of the feeding, the reactor was cooled, and the liquid remaining in the reactor was withdrawn and quantitatively analyzed by GC. As perfluoroalkyl iodides except for unreacted $CF_3CF_2I$, 52% of $CF_3(CF_2)_3I$, 29% of $CF_3(CF_2)_5I$ and 19% of $CF_3(CF_2)_7I$ were detected.

According to the production method of the present invention, a reaction which otherwise accompanies a side reaction of the desired compound with the feedstock compound, is carried out in a distillation column portion, whereby the desired compound can be obtained at a high conversion and high selectivity. The production method of the present invention is a method which can be carried out without requiring special conditions or reagents, and it is a highly practical method which can be used as an industrial production method of a large capacity. The method of the present invention is a method which is excellent in the volume efficiency and suitable for mass production and thus is useful as an industrial production method of a large capacity.

What is claimed is:

1. A method for producing a fluorine-containing hydroxyl compound, which comprises reacting a fluorine-containing unsaturated compound of the following formula (1) and a hydroxyl compound of the following formula (2) in the presence of a free radical initiator to obtain a fluorine-containing hydroxyl compound of the following formula (3), wherein the reaction is carried out under reflux in a distillation column portion of a reactor provided with the distillation column:

  (1)

  (2)

  (3)

wherein $R^f$ is a monovalent fluorine-containing organic group having from 1 to 20 carbon atoms, Q is a single bond or a bivalent linking group selected from the group consisting of a bivalent $C_{1-8}$ hydrocarbon group and, a bivalent $C_{1-8}$ alkylene group and each of $R^1$ and $R^2$ which are independent of each other, is a hydrogen atom or an alkyl group having from 1 to 5 carbon atoms, provided that the sum of the carbon numbers in $R^1$ and $R^2$ is from 0 to 5.

2. The method according to claim 1, wherein the reaction is carried out while continuously supplying the fluorine-containing unsaturated compound of the formula (1), the hydroxyl compound of the formula (2) and the free radical initiator to the distillation column portion wherein the hydroxyl compound of the formula (2), or the hydroxyl compound of the formula (2) and the free radical initiator, are refluxed.

3. The method according to claim 1, wherein the reaction is carried out while continuously supplying the fluorine-containing unsaturated compound of the formula (1) so that the residence time of the fluorine-containing unsaturated compound in the distillation column portion will be from 1 to 60 minutes.

4. The method according to claim 2, wherein the fluorine-containing hydroxyl compound of the formula (3) is continuously withdrawn from a lower portion of the reactor.

5. The method according to claim 1, wherein the free radical initiator is an organic compound having a boiling point of not higher than the reaction temperature, an organic compound azeotropically distillable together with the fluorine-containing unsaturated compound of the formula (1) and/or the hydroxyl compound of the formula (2), or an organic compound having a half-life of greater than zero minutes to at most 10 minutes at the reaction temperature.

6. The method according to claim 1, wherein the hydroxyl compound of the formula (2) is methanol, ethanol or isopropanol.

7. The method according to claim 1, wherein $R^f$ is a perfluoroalkyl group having from 2 to 8 carbon atoms.

8. The method according to claim 1, wherein Q is a single bond or an $C_{1-5}$ alkylene group.

9. The method according to claim 2, wherein the free radical initiator is an organic compound having a boiling point of not higher than the reaction temperature, an organic compound azeotropically distillable together with the fluorine-containing unsaturated compound of the formula (1) and/or the hydroxyl compound of the formula (2), or an organic compound having a half-life of greater than zero minutes to at most 10 minutes at the reaction temperature.

10. The method according to claim 2, wherein the hydroxyl compound of the formula (2) is methanol, ethanol or isopropanol.

11. The method according to claim 2, wherein $R^f$ is a perfluoroalkyl group having from 2 to 8 carbon atoms.

12. The method according to claim 2, wherein Q is a single bond or an alkylene group.

13. The method according to claim 5, wherein said half-life is from 1 to 10 minutes.

14. The method according to claim 9, wherein said half-life is from 1 to 10 minutes.

15. The method according to claim 5, wherein the free radical initiator organic compound having a half-life of greater than zero minutes to at most 10 minutes at the reaction temperature is a peroxy organic compound or an azo organic compound.

16. The method according to claim 15, wherein said peroxy organic compound is selected from the group consisting of an alkylhydroperoxy compound, a dialkylperoxy compound, a peroxy ketal, a diacylperoxy compound, a peroxy carboxylic acid ester, a peroxy carboxylic acid, and a peroxy carbonate.

* * * * *